(12) United States Patent
Gopal

(10) Patent No.: US 9,697,994 B1
(45) Date of Patent: Jul. 4, 2017

(54) USE OF STABLE LABEL COMPOUNDS WITH ACCELERATOR MASS SPECTROMETRY

(71) Applicant: Damodaragounder Gopal, Highlands Heights, OH (US)

(72) Inventor: Damodaragounder Gopal, Highlands Heights, OH (US)

(73) Assignee: Ricarez Biosciences, LLC, Concord, OH (US)

( * ) Notice: Subject to any disclaimer, the term of this patent is extended or adjusted under 35 U.S.C. 154(b) by 0 days.

(21) Appl. No.: 14/999,197

(22) Filed: Apr. 8, 2016

(51) Int. Cl.
*G01N 33/53* (2006.01)
*C12Q 1/68* (2006.01)
*A01N 43/04* (2006.01)
*H01J 49/00* (2006.01)

(52) U.S. Cl.
CPC ............................. *H01J 49/0027* (2013.01)

(58) Field of Classification Search
USPC ........ 435/4, 6.1, 6.11; 514/2.1, 5.8, 5.9, 6.1, 514/6.2, 6.3, 6.4, 6.5, 44 R, 44 A
See application file for complete search history.

(56) References Cited

U.S. PATENT DOCUMENTS

| | | |
|---|---|---|
| 3,627,487 A | 12/1971 | Jepson et al. |
| 6,071,245 A | 6/2000 | Kohne et al. |
| 6,355,416 B1 * | 3/2002 | Abramson ............... C12Q 1/68 |
| | | 435/6.12 |
| 2012/0190560 A1 | 7/2012 | Hellerstein |
| 2014/0295485 A1 * | 10/2014 | Hellerstein ........ G01N 33/5088 |
| | | 435/34 |

FOREIGN PATENT DOCUMENTS

WO   WO 2005 029039 A2 *   3/2005

OTHER PUBLICATIONS

Sean L. Kitson, Accelerated Radiochemistry, www.Researchgate.net, Mar. 2010.
Xceleron, The Power of AMS, www.xceleron.com/thepowerofams.

* cited by examiner

*Primary Examiner* — Bernard Souw
(74) *Attorney, Agent, or Firm* — Timothy E. Tinkler

(57) ABSTRACT

Disclosed herein is a method for evaluating and measuring the performance, efficacy and safety of candidate new chemical entities. This method comprises employing a target compound having one or more $^{12}C$ atoms in the molecule wherein at least one of the $^{12}C$ atoms is substituted with a $^{13}C$ atom, The stable labelled target compound is then administered to a test subject following which the target compound and/or one or more of its metabolites are recovered using conventional separation techniques and purified. The resulting isolated material of interest is then combusted in the presence of a petrochemical based carrier, the $^{12}C$ content of such carrier with respect to naturally occurring $^{13}C$ being in excess of 99.9 percent. The $CO_2$ resulting from such combustion is then graphitized and the graphitized material is analyzed employing techniques, such as Accelerator Mass Spectrometry ("AMS"), capable of differentiating and counting the carbon atom isotopes ($^{13}C$ vs. $^{12}C$), thus allowing quantification of the compound/metabolite of interest.

5 Claims, No Drawings

USE OF STABLE LABEL COMPOUNDS WITH ACCELERATOR MASS SPECTROMETRY

CROSS REFERENCE TO A RELATED APPLICATION

This application claims the benefit of U.S. Provisional Application 62/178,420 filed Apr. 9, 2015, which is expressly incorporated by reference herein.

BACKGROUND

Currently, for example to help researchers attempting to evaluate the performance, mechanisms of operation and safety of new chemical entities, as is generally required to obtain regulatory approval of the use of such target compounds in commerce, radiolabelled analogues are prepared and employed. Often this involves the in vivo administration of a radiolabelled version of the so called tracer compound to help understand the distribution, flux, metabolic fate and tissue concentration of the compound during the course of preclinical and environmental studies. Various analytical techniques allow the researcher to know how much of and over what period of time the applied tracer compound is excreted. Just as importantly, the metabolites can be traced and measured to determine if safety issues might exist as a result of administration of the compound.

The label of choice is commonly $^{14}C$, which replaces one or more of the $^{12}C$ atoms in the molecule under study. The radioisotope is rare in nature so its presence can readily be attributed to the labelled compound under study. Half-life of the isotope is long enough that there is no concern regarding the possible biological effect of its presence and it can be inserted into the carbon frame work of the target compound without altering its chemical structure. However, there are numerous problems associated with the use and handling of radiolabelling isotopes. The supply of radiolabelled raw materials is limited and their cost is high. Such isotopes are tightly regulated and disposal of waste materials is also regulated and expensive. While the half-life of $^{14}C$ for example is extended, the energy related to its decay can lead to radiolytic instability of the candidate compound causing a reduction in purity with time. Thus a need exists for an alternative to the use of radiolabelled compounds to meet at least a portion of the research and regulatory requirements surrounding the development and commercialization of new, biologically active compounds for use as pharmaceuticals, agrochemicals, veterinary compounds and the like.

BRIEF DESCRIPTION

In order to overcome the disadvantages associated with the use of radiolabelled compounds to obtain information to evaluate and measure the performance, efficacy and safety of candidate new chemical entities, a method for doing so using stable labelled analogues of such entities is disclosed herein. This method comprises employing a target compound having one or more $^{12}C$ atoms in the molecule, wherein at least one of the $^{12}C$ atoms has been substituted with a $^{13}C$ atom. The resulting stable labelled target compound is then administered to a test subject following which the target compound and/or one or more of its metabolites are recovered using conventional separation techniques and purified. The resulting isolated material of interest is then combusted in the presence of a carbon based carrier, the $^{12}C$ content of such carrier with respect to naturally occurring $^{13}C$ being in excess of 99.9 percent. The degree of $^{12}C$ purity of the carrier will be somewhat dependent upon the number of $^{13}C$ labels applied to the target compound and the level of quantification required, fewer labels for example requiring higher $^{12}C$ purity. The $CO_2$ resulting from such combustion is then graphitized and the graphitized material is analyzed employing techniques, such as Accelerator Mass Spectrometry ("AMS"), capable of differentiating and counting the carbon atom isotopes ($^{13}C$ vs. $^{12}C$), thus allowing quantification of the compound/metabolite of interest.

These and other features and advantages of the invention will become apparent from the discussion and description set forth below.

DETAILED DESCRIPTION

The science of attaching labels, both stable and radioactive, is highly specialized owing to the diversity of materials that are candidates for such labelling. Generally speaking however, the use of stable labels such as $^{13}C$, presents fewer problems. In connection with the drug industry for example, a wide variety of candidates, large and small molecule, and intermediates are being proposed and each requires special considerations, for example regarding the location and number of labels to be attached without altering the chemical structure of the molecule. Teams of specially trained and experienced scientists both within the pharma industry and in custom radiolabelled synthesis contract laboratories have come into being to meet the growing requirements for such services. Those skilled in the art will understand that the scope of this invention does not relate to the various synthesis techniques that are known or must be developed, rather to the process that follows and allows the testing and quantification of the target material, once labelled with one or more $^{13}C$ atoms.

Once synthesized, the labelled material will generally be employed by in vivo administration to a test subject with the objective of potentially determining virtually every aspect of the material's behavior in vivo or in any other applied environment (plants, soil, etc.). In this manner, a variety of safety and efficacy information may be obtained. For example a drug candidate may be used in preclinical studies to evaluate the absorption, distribution, metabolism, excretion and toxicology (ADMET) profile.

Following application of the labelled material, depending upon the nature of the evaluation being conducted, the material and/or its metabolites may be separated from the test subject by conventional means such as chemical extraction and chromatographic separation specific to the nature of the substrate and the material to be further analyzed. Conventionally the target analyte containing the $^{14}C$ labelled compound or metabolite would then be analyzed, for example by decay counting, to determine the amount of $^{14}C$ present, for comparison to total $^{14}C$ in the applied labelled material.

Recently, an analytical platform known as Accelerator Mass Spectrometry ("AMS") has been developed which, owing to its high sensitivity (that is, its power to separate a minor amount of one isotope from an abundant neighboring mass, e.g., $^{14}C$ from $^{12}C$), allows the use of increasingly small amounts of $^{14}C$ radiolabelled material while still obtaining meaningful results. Indeed it has been proposed that the sensitivity of the AMS technology may allow relatively risk free "microdosing" of human subjects to allow the study of the candidate material in the ultimately intended target. Simply put, the AMS platform entails combusting (oxidizing) the purified target analyte in the presence of relatively large quantities of a petrochemical based organic carrier such as benzoic acid. The resultant $CO_2$ is then graphitized by known methods and the AMS instrument ionizes the graphitized sample. The $^{12}C$, $^{13}C$ (naturally occurring) and $^{14}C$ ions are separated and counted, using separate detectors the most sensitive of which is able to count individual $^{14}C$ ions. These results can then be compared to the specific radioactivity of the target analyte and the total carbon content of the graphitized sample. However, the problems associated with radiolabelled materials, such as synthesis, expense, storage, handling and disposal, continue.

The present invention builds upon the conventional process by recognizing that, with the application of appropriate improvements, the advantages provided by the sensitivity of the advanced AMS technology can be used to allow the use of stable labelled isotopes, particularly $^{13}C$, in place of the radiolabel(s), such as $^{14}C$. A simple substitution of labels is not possible owing to the fact that, while $^{14}C$ is quite rare in nature (less than one atom in a million), $^{13}C$ is much more prevalent being naturally present on the order of 1.1%. While still small relative to the $^{12}C$ present in organic compounds, the amount of carbon attributed to the $^{13}C$ naturally present in the carrier and the test material, would obscure that contributed by a $^{13}C$ stable label. However, it has now been found that use of a carrier with the AMS platform that has a $^{12}C$ purity in excess of 99.9%, preferably more than 99.99% and for some applications 99.999% or more, coupled with the sensitivity realized by the AMS technology, allows detection of the stable label with sufficient sensitivity for many purposes now only capable of being realized with the use of radioisotopes. Further, the degree of purity of $^{12}C$ required can be controlled by increasing the number of $^{13}C$ labels incorporated in the material to be evaluated, thus increasing the ability to detect and differentiate the $^{13}C$ attributable to the labelled material versus background.

Although the disclosure has been described with respect to specific embodiments, it is not intended to be limited thereto. It will be understood by those skilled in the art that various changes in the steps, details, materials and the like which have been herein described in order to explain the nature of the invention may be made while remaining within the spirit of the disclosure and the scope of the claims.

The invention claimed is:

1. A process for the tracing and quantification of metabolites or other breakdown products of target compounds without the use of radiolabels which comprises:
    employing a target compound on which one or more of $^{12}C$ carbons has been substituted with $^{13}C$ carbons,
    administering the $^{13}C$ labeled target compound to a test subject,
    separating and purifying the parent compound and one or more metabolites of interest from the test subject by conventional separation techniques,
    combusting the purified compound of interest in the presence of a carrier having a $^{12}C$ purity of at least 99.9% and graphitizing the resultant $CO_2$ and
    subjecting the graphitized material to analysis by Accelerator Mass Spectrometry to quantify the amount of $^{13}C$ present in the sample.

2. A process as in claim 1, wherein greater than one $^{12}C$ carbon has been substituted with a $^{13}C$ carbon.

3. A process as in claim 1 wherein the carrier is benzoic acid.

4. A process as in claim 1 wherein the carrier has a $^{12}C$ purity of at least 99.99%.

5. A process as in claim 1 wherein the carrier has a $^{12}C$ purity of at least 99.999%.

* * * * *